(12) United States Patent
Wolfinbarger

(10) Patent No.: US 6,416,995 B1
(45) Date of Patent: Jul. 9, 2002

(54) BIOREACTOR MEDIATED RECELLULARIZATION OF NATURAL AND TISSUE ENGINEERED VASCULAR GRAFTS

(75) Inventor: Lloyd Wolfinbarger, Norfolk, VA (US)

(73) Assignee: Bio Science Consultants, L.L.C., Norfolk, VA (US)

( * ) Notice: Subject to any disclaimer, the term of this patent is extended or adjusted under 35 U.S.C. 154(b) by 0 days.

(21) Appl. No.: 09/714,815

(22) Filed: Nov. 17, 2000

Related U.S. Application Data

(63) Continuation of application No. 09/595,717, filed on Jun. 16, 2000.
(60) Provisional application No. 60/166,884, filed on Nov. 22, 1999.

(51) Int. Cl.⁷ .............................................. C12M 3/00
(52) U.S. Cl. ................... 435/289.1; 435/297.2; 435/284.1; 623/916; 623/921
(58) Field of Search ................... 435/1.1, 284.1, 435/289.1, 297.2, 297.4, 307.1; 623/1.41, 916, 917, 921

(56) References Cited

U.S. PATENT DOCUMENTS

| | | | |
|---|---|---|---|
| 4,083,066 A | * | 4/1978 | Schmitz et al. |
| 4,546,500 A | * | 10/1985 | Bell |
| 4,908,013 A | * | 3/1990 | Muller et al. |
| 4,911,713 A | * | 3/1990 | Sauvage et al. |
| 5,376,110 A | * | 12/1994 | Tu et al. |
| 5,387,236 A | * | 2/1995 | Noishiki et al. |
| 5,613,982 A | * | 3/1997 | Goldstein |
| 5,792,603 A | * | 8/1998 | Dunkelman et al. |
| 5,916,265 A | * | 6/1999 | Hu |
| 5,916,800 A | * | 6/1999 | Elizondo et al. |

FOREIGN PATENT DOCUMENTS

WO      WO-93/01843 A1 * 2/1993

* cited by examiner

Primary Examiner—William H. Beisner
(74) Attorney, Agent, or Firm—W. Jackson Matney, Jr.; Milbank, Tweed, Hadley & McCloy LLP

(57) ABSTRACT

The invention provides a device and process for recellularizing essentially acellular or devitalized tissue grafts, including for example essentially acellular or devitalized vascular tissue grafts, derived from human or animal sources, or as constructed using any number of tissue engineering methodologies. The process includes repopulating and reendothelializing an essentially acellular or devitalized tissue graft. The device is useful for producing a repopulated tissue graft from an essentially acellular or devitalized tissue, as well as for producing an essentially acellular or devitalized tissue graft.

42 Claims, 9 Drawing Sheets

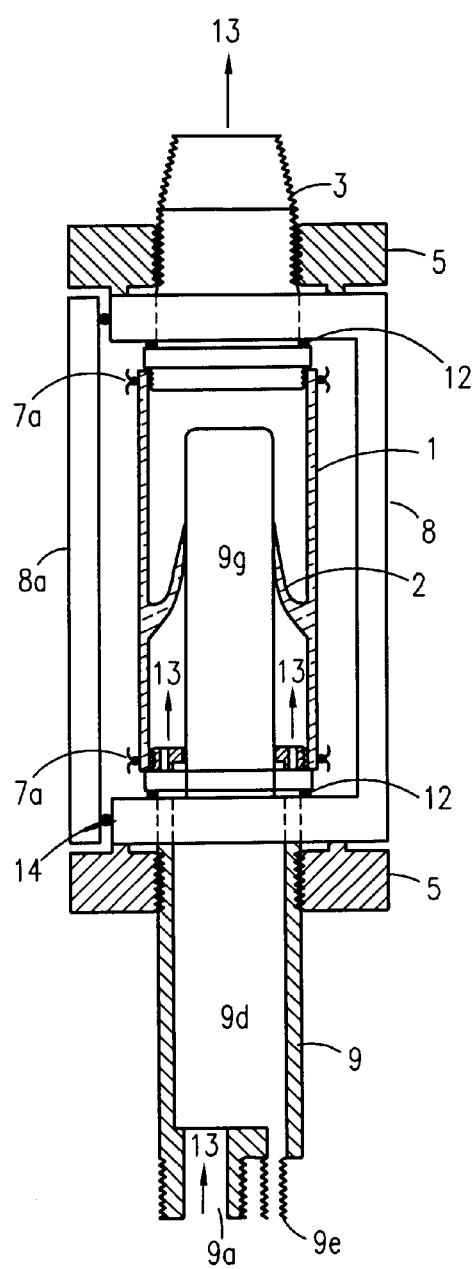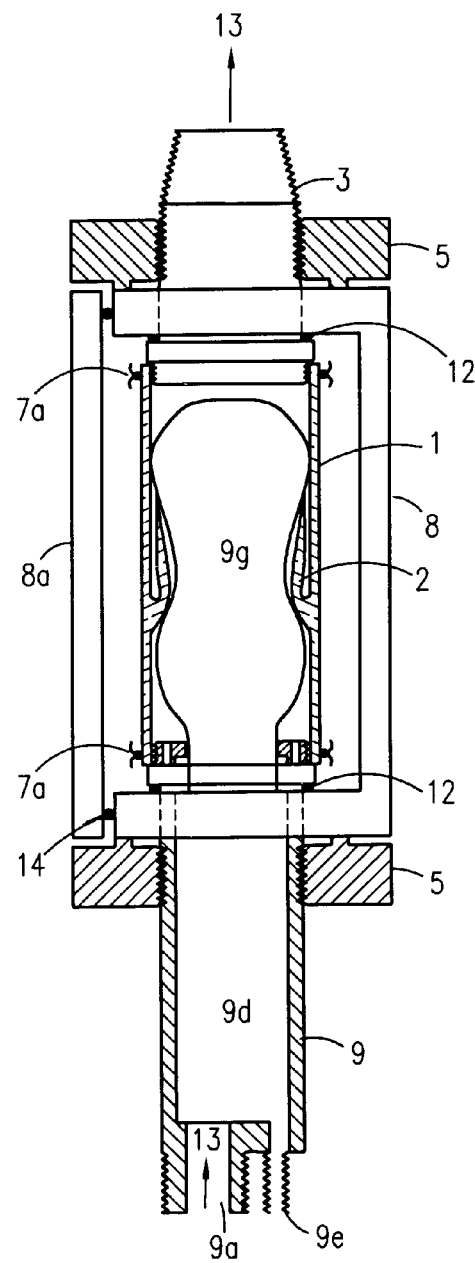
Fig. 10
Fig. 11

BIOREACTOR MEDIATED RECELLULARIZATION OF NATURAL AND TISSUE ENGINEERED VASCULAR GRAFTS

This application is a continuation of U.S. patent application Ser. No. 09/595,717, filed Jun. 16, 2000, and claims the benefit of U.S. patent application Ser. No. 60/166,884, filed Nov. 22, 1999.

FIELD OF THE INVENTION

A variety of vascular grafts are commercially available and include mechanical, bioprosthetic, and cryopreserved and decellularized human and animal heart valves. In addition, non-valved vascular grafts made of expanded polytetrafluoroethylene (ePTFE), decellularized veins and arteries, and cryopreserved veins and arteries are available. Vascular grafts constructed from naturally occurring molecules, for example collagens, elastins, hyaluronins, etc. can be manufactured using tissue engineering techniques. Such vascular grafts, whether valved or non-valved can be used in clinical applications in an essentially cellularized on decellularized state. The current invention is directed at providing a device and process for recellularizing essentially acellular, i.e. avital, vascular grafts derived from human or animal sources or as constructed using any number of tissue engineering methodologies.

BACKGROUND OF THE INVENTION

Vascular grafts include a wide variety of natural and synthetic tubular structures that may or may not contain valves. Valves in these tubular structures are usually intended to direct the flow of blood (or other nutrient materials) in one direction by preventing the backward flow of this (these) liquid solution(s). Examples of valved tubular structures include aortic, pulmonary, and mitral valves present in the hearts of most vertebrate animals and veins used to return blood flow from the periphery of the body to the heart for recirculation. Vascular grafts constructed of synthetic materials include devices constructed from man-made polymers, notably Dacron and Teflon in both knitted and woven configurations such as those marketed by W. L. Gore, Inc. and Impra, Inc. where various forms of polytetrafluoroethylene (PTFE) are molded into a wide array of tubule structures (see for example U.S. Pat. Nos. 4,313,231; 4,927,676; and 4,655,769). The present invention does not involve vascular grafts derived from synthetic means and thus these types of vascular grafts will not be further discussed. Natural vascular grafts, taken in the context of this present invention, include valved and non-valved tubular structures obtained by methodologies broadly classified under the term "tissue engineering". Notably, tissue engineered blood vessels such as described in U.S. Pat. Nos. 4,539,716, 4,546,500, 4,835,102, and blood vessels derived from animal or human donors such as described in U.S. Pat. Nos. 4,776,853, 5,558,875, 5,855,617, 5,843,181, and 5,843,180, and a pending patent application entitled "A Production Technology for Commercial Scale Decellularization Processing of Soft-Tissue Engineered Medical Implants" (patent application Ser. No. 09/528,371 incorporated herein in its entirety) are known. The present invention involves vascular grafts derived using a specific process associated with tissue engineering as well as a bioreactor device to be used in this process.

Tissue engineered natural vascular grafts, hereinafter vascular grafts, can be manufactured by processing of natural vascular grafts (veins, arteries, heart valves, etc.) with the objective of removing the cellular elements without damaging the matrix structure of that tissue-a "reductionist" approach. This approach is generally referred to as decellularization and is the subject of several patents, of which U.S. Pat. No. 4,801,299 by Brendel and Duhamel is considered as one of the earliest such patents, and pending patent applications as described above. Decellularization of tissues such as vascular grafts can be readily accomplished by incubating tissues in the presence of detergents, both anionic and nonionic, with and without digestion of nucleic acids using DNase and RNase enzymes, or more recently a commercially available recombinant endonuclease called Benzonase™. The decellularized tissues typically retain the structurally important molecules such as collagens, elastins, proteoglycans, and associated polysaccharides such as the hyaluronins, (see U.S. Pat. No. 5,855,620 as an example). Specifically, the Brendel & Duhamel patent (U.S. Pat. No. 4,801,299) defines decellularization as "A method of treating body tissue to remove cellular membranes, nucleic acids, lipids, and cytoplasmic components and form extracellular matrix having as one major component collagens and making said body tissue suitable for use as a body implant . . . " The Klement, Wilson, and Yeger patent (U.S. Pat. No 4,776,853) defines decellularization as "A process for preparing biological material for implant in a mammal's cardiovascular system, respiratory system or soft tissue by removing cellular membranes, nucleic acids, lipids, and cytoplasmic components and forming an extracellular matrix having as major components collagens and elastins . . . " A devitalization process/method (i.e. producing an avital tissue) would be defined for purposes of the present invention as a process or method of treating body tissue to remove cellular membranes, nucleic acids, lipids, and small molecular weight cytoplasmic components forming an extracellular matrix having as one major component collagens, elastins, and high molecular weight polysaccharides. By leaving the high molecular weight cytoplasmic molecules, for example actins, complete decellularization would not be obtained and the tissue would be considered to be devitalized. In specific instances, patented technologies have suggested that such decellularized vascular grafts can function for extended periods of time following clinical implantation without the need for recellularization. Indeed some such technologies have treated tissues with high concentrations of the anionic detergent sodium docecylsulfate (SDS) to attempt to prevent recellularization of implanted vascular grafts (U.S. Pat. Nos 4,776,853 and 5,558,875).

Tissue engineered natural vascular grafts have also been constructed using a "constructionist" approach. This approach involves the extraction of natural cellular and matrix components to obtain purified (or partially purified) fractions and then using these fractions to reconstruct a vascular graft from individual components. Alternatively, specific components of a vascular graft, for example collagen(s), can be obtained using recombinant DNA technologies and such highly purified and homogeneous materials used in the construction of natural vascular grafts via tissue engineering. Methods and materials for 3-dimensional cultures of mammalian cells are known in the art. See, e.g., U.S. Pat. No. 5,266,480. Typically, a scaffold is used in a bioreactor growth chamber to support a 3-dimensional culture, see for example U.S. Pat. No. 6,008,049. The scaffold can be made of any porous, tissue culture compatible material(s) into which cultured mammalian cells can enter and attach.

Both the reductionist and constructionist approaches are designed to provide an acellular matrix (unless the constructionist approach also intends to incorporated living cells in the matrix during the construction of the tissue engineered vascular graft) that can be used directly as an acellular graft. Alternatively the acellular matrix can be reseeded with specific cell populations to provide a recellularized graft (see for example, U.S. Pat. Nos. 5,792,603; 5,613,982; 5,855, 617; 5,843,180; 5,843,181; and 5,843,182). One U.S. Pat. No. 5,855,617 describes the use of fibroblast growth factor to attract fibroblast cells to migrate into a substantially non-immunogenic vascular graft.

Vascular tissues such as an aortic heart valve contain a limited number of cell types. For aortic valves, these cell types include endothelial cells that line the luminal surface of the valve providing for a smooth, non-thrombogenic, surface for efficient blood flow. These cells are known for their role in nitric oxide (a vasodilating agent), expression of vasoconstricting endothelins, and smooth muscle proliferative mitogens and cytokine (Interleukin-1, tumor necrosis factor, Interleukin 6, Interleukin 8, Monocyte Chemoattractant protein-1, granulocyte monocyte-CSF, and Monocyte chemoattractant and stimulating factor) production. These endothelial cells are attached to a thin basement membrane that is comprised essentially of high density, i.e. minimal porosity, type IV collagens. The basement membrane is visible, following removal of endothelial cells, as a smooth surface essentially devoid of breaks in integrity and closely following the topography of the underlying vascular structure. Within the underlying vascular structure, the cellular elements primarily consist of a fibroblastic cell population, typically referred to as myofibroblasts in that their origin is described as being muscle and specifically cardiac muscle and smooth muscle cells. This fibroblastic cell population has been described as being an important element to the continued repair and synthesis of the molecular elements comprising the heart valve matrix. Of relevance to this present invention are observations such as:

1) The basement membrane lining the luminal surface of a vascular graft is essentially impenetrable by cells due to its high density of structural elements, i.e. minimal porosity to cells due to small openings in the matrix structure;

2) The small dimensions of pores present in the matrix structure of the basement membrane are too small for cells to easily penetrate;

3) Type IV collagen has been described as being inhibitory to cellular proliferation in in vitro, such studies suggesting a strong potential to chemically inhibit trans-membrane migration of cells;

4) Endothelial cells and matrix fibroblasts communicate via a paracrine (local) chemical signaling process, where this signaling is important to the continued function and well-being of both cell populations;

5) Transplanted, cryopreserved, human heart valves containing viable fibroblastic cell populations at the time of transplantation into a patient have been reported to be devoid of viable fibroblastic cells in as little as a few months post transplantation, supportive of the concept of an important paracrine signaling function between cells of a native valve and an inductive process of apoptosis;

6) Transplanted, cryopreserved, human heart valves continue to function for as long as 20 years post transplantation in spite of the loss of both the endothelial and fibroblastic cell populations, suggesting that the absence of a viable fibroblastic cell population may be of minimal importance to long-term function of an aortic valve;

7) Transplanted, cryopreserved, human heart valves recellularize only poorly by recipient fibroblastic cells post transplantation, suggesting an inherently poor inducement by the transplanted tissue for cells to migrate into the matrix structure of a cardiovascular graft; and 8) Transplanted, cryopreserved, human heart valves reendothelialize only poorly by recipient endothelial cells post transplantation and where reendothelialization occurs, it is primarily at the surgical anastomoses.

Collectively, these published observations tend to suggest that simple incubation of fibroblastic cells with cardiovascular tissues will result in successful cellular penetration into the matrix structure only via the adventitial (outside) surface of the vascular graft. Such penetration will most likely require some inducement other than simply incubating cells with this surface hoping the cells will attach to the adventitial surface and migrate into the tissue. Penetration of fibroblastic cells into the tissue matrix via the luminal surface will require partial or complete removal of the basement membrane, or strategic perforation of the basement membrane. In that cardiovascular tissues where the basement membrane remain intact mostly fail to recellularize by recipient cells post-transplantation would seem to suggest that recellularization without inducement is an unlikely event. In addition, the high flow-fields (high rates of blood flow through an aortic valve) or an inherent inability of endothelial cells to migrate along the surface of the basement membrane tends to suggest that reendothelialization of a vascular graft will require more than simple incubation of endothelial cells in suspension cultures with a vascular graft. Some effort will need to be made to attach and align the endothelial cells such that the flow of fluids across their surfaces will not tend to detach them until they have had an opportunity to align themselves post seeding. Such alignment will presumably require pulsatile fluid flow to mimic in situ conditions for endothelial cell function. U.S. Pat. No. 5,928,945 describes the tissue engineered production of cartilage where shear flow stress of about 1 to about 100 dynes/cm$^2$ produce artificial cartilage when cells are grown in a bioreactor on an artificial substrate.

U.S. Pat. No. 5,792,603 (hereinafter "patent 603") entitled "Apparatus and method for sterilizing, seeding, culturing, storing, shipping and testing tissue, synthetic or native, vascular grafts" describes a bioreactor mediated apparatus and method for sterilizing, seeding, culturing, storing, shipping, and testing vascular grafts. This patent differs from the present invention in several important aspects.

1) Patent 603 describes alternating pressure to a support structure within the treatment chamber upon which a vascular graft scaffold is positioned. The present invention describes alternating pressure to a vascular graft within the treatment chamber and there is no associated support structure.

2) Patent 603 describes applying a radial/shear stress on the scaffold where the associated vascular graft scaffold and associated formed vascular graft is/are attached at one end and discharges solution flow directly into the treatment chamber such that the pulsatile pressure is not contained within the lumen of the scaffold/vascular graft. The present invention describes applying a radial/shear stress on the vascular graft where the vascular graft is attached to the treatment chamber (bioreactor) such that solution flow induced radial stress is controllable by regulating pressure between the advential side of the vascular graft and the inner wall of the treatment chamber and pulsatile pressure is contained within the lumen of the vascular graft.

3) Patent 603 relies on cellular ingrowth into the formed vascular graft supported by the vascular graft scaffold from the nutrient solutions being pumped through the lumen of the formed vascular graft and into the treatment chamber prior to this solution plus cells exiting the treatment chamber for recirculation to the treatment chamber. The present invention relies on a pressure differential between the luminal side and adventitial side of the vascular graft, generated by closing the outflow port of the luminal volume of the graft and opening the outflow port of the treatment chamber (bioreactor) associated with the volume outside of the luminal volume of the vascular graft. This pressure differential causes cells to move with solution flow across the volume of the tissue, luminal surface to adventitial surface, comprising the vascular graft such that the cells become entrapped within the matrix volume of the vascular graft.

4) Patent 603 does not control the volume of the luminal volume of formed vascular grafts. The present invention utilizes an inflatable piston to control the volume of the luminal volume of vascular grafts.

5) Patent 603 generates radial and/or shear stresses within the formed vascular grafts without controlling the stress (for example: force per unit cross-sectional area) and strain (for example: deformation from the unstressed state) on the formed vascular graft. The present invention allows control of the stress and strain on the vascular graft during the recellularization and preconditioning stages of the process in that the graft is attached at both ends to inflow and outflow ports and graft deformation during pulsatile pressure mediated flow of solutions can be controlled by management of the volume of solution between the advential (out) side of the vascular graft and the inner wall of the treatment chamber.

Based on these differences, it is suggested that the present invention is dramatically different from Patent 603 in the manner in which cells are induced to repopulate the vascular graft and in radial and shear stresses used to induce the cells repopulating the graft to experience physiologically relevant mechanical forces. The present invention, by being able to control stress and strain values applied to the vascular graft permit a more physiological and mechanically relevant conditions within the recellularized vascular graft(s). The manner in which the vascular grafts are attached in the treatment chamber (bioreactor) are significantly different between Patent 603 and the present invention. In Patent 603 the graft is attached at one end whereas in the present invention, the graft is attached at both ends.

The present invention is designed to take advantage of knowledge gained from prior art without actually incorporating prior art into the invention. The present invention provides a bioreactor approach to reseeding of vascular grafts, such as a decellularized aortic heart valve. The approach involves removal of the basement membrane by enzymatic digestion. This removal of basement membrane is followed by pressure-differential induced movement of fibroblastic cells in a solution into the matrix structure and reendothelialization by incorporation of endothelial cells into a collagenous/noncollagenous solution. This latter solution is compacted, as necessary, by "pressure" binding of this mixture onto the luminal surface to recreate a "basement membrane" containing endothelial cells. Cells are induced to resume metabolic activities following treatment with specific growth factors, for example fibroblast growth factor, or platelet aggregation under a pulsatile flow of nutrient solutions. The novel design of the bioreactor facilitates the processes described in the present invention.

Definitions

As used herein, "recellularization" means the repopulation of the matrix volume of a tissue engineered or devitalized-essentially acellular/decellularized-acellular matrix structure with a viable cell population that is either the desired cell phenotype and/or genotype or that which can be caused to differentiate into the desired cell phenotype and/or genotype.

As used here in, "nonvital" means tissue that has been treated to inactive the metabolic and/or reproductive capacity of cells residing within the tissue or residing on the luminal/adventialial surface(s) of the tissue(s). The cells are not necessarily disrupted and/or solubilized and may be visibly discernable using standard histological means and standard microscopic techniques known to persons skilled in the art. Alternatively, nonvital (or devitalized tissue) could mean tissue that has been treated to remove essentially all of the visible cellular remnants leaving only high molecular weight cytoplasmic moleculars such as, for example, actins.

As used herein, "reendothelialization means the repopulation of the flow surface of a tissue engineered or decellularized-acellular matrix structure with a metabolically and reproductively viable endothelial cell population that is either phenotypically and/or genotypically an endothelial cell at the time of repopulation or that which can be caused to differentiate into the desired cell phenotype and/or genotype.

As used herein, "decellularization" means the removal of cells and cell remnants from a tissue matrix structure using liquid solution processing such that cells are not visibly present, using standard microscopic techniques, in standard histologic preparations.

As used herein, "cell to cell communication" means the chemical and/or physical signaling between one or more cells and/or cell populations such that a given cell or cell population is stimulated to function in a manner necessary to the role of that cell in maintaining tissue function. This cell to cell communication can occur by paracrine types of signaling using large and small molecular weight factors and is generally restricted to within the tissue comprising the functional entity being observed or studied.

Unless otherwise defined, all technical and scientific terms used herein have the same meaning as commonly understood by one skilled in the art of tissue processing and cell culturing techniques. Although materials and methods similar or equivalent to those described herein can be used in the practice or testing of the invention, the preferred methods and materials are described below. All publications, patent applications, patents and other references mentioned herein are incorporated by reference. In addition, the materials, methods, and examples are illustrative only and not intended to be limiting.

SUMMARY OF THE INVENTION

According to one aspect of the present invention, a device and process is described for recellularizing and reendothelializing essentially acellular vascular grafts for use in replacement of defective heart valves and vascular conduits. The device is a bioreactor designed to facilitate selected steps in the processing such as recellularization and reendothelialization. The process includes several steps which may be conducted outside of the bioreactor and several steps which may be conducted inside of the bioreactor such that most of the invention is carried out in a closed processing system that will dramatically restrict contamination by microbiological and chemical/biological elements. In one preferred aspect, the process comprises the following steps:

1) use of an essentially acellular or non-vital vascular graft, such as a heart valve, whether constructed as an acellular graft using tissue engineering methods or decellularizing and/or devitalizing a native vascular graft using methods known in the art;
2) attaching the acellular/devitalized graft into the bioreactor by attaching the graft directly to the inlet and outlet port connections or by sewing/attaching the graft to sewing rings and attaching the sewing rings to the inlet and outlet port connections and closing the unit as illustrated in the attached figures;
3) optionally treating the acellular graft with various growth and/or differentiation factors, such as fibroblast growth factor (FGF), polylysine, hyaluronins, proteoglycans, RGD-containing peptides, sodium dodecylsulfate, sodium dodecylsarcosinate, or suramin, to achieve binding in the tissue matrix;
4) washing the acellular or devitalized graft with an appropriate aqueous solution to remove unbound, or loosely bound growth and/or differentiation factors;
5) debriding the basement membrane using proteolytic enzymes, for example dispase and/or collagenase, to achieve total or partial removal of the basement membrane lining the luminal surface of the acellular graft;
6) washing the acellular or devitalized graft with an appropriate aqueous solution to remove excess proteolytic enzymes;
7) seeding the acellular graft or devitalized graft with a fibroblastic cell population, allogenously or autogenously derived, using a positive pressure mediated infusion of cells into the tissue matrix spaces;
8) washing the recellularized graft with an appropriate iso-osmotic solution such that only the luminal volume and the volume outside of the vascular graft are replaced and no additional pressure flow occurs across the matrix of the recellularized graft;
9) seeding the recellularized graft with an endothelial cell population, allogenously or autogenously derived, using a viscous collagenous/noncollagenous mixture containing the endothelial cells;
10) partially pressurizing the luminal volume to compress the viscous collagenous/noncollagenous/endothelial cell mixture onto the luminal surface of the now recellularized and reendothelialized graft;
11) washing the now recellularized and reendothelialized graft to remove excess viscous collagenous mixture;
12) applying a slow pulsatile flow of nutrient rich and growth factor containing medium, optionally containing allogenous or autogenous platelets, to establish a functionally viable cell population in the graft such that the fibroblastic cell population and the endothelial cell population establish a viable vascular graft;
13) applying a pulsatile flow of nutrient rich medium at a flow rate appropriate to provide a stress field in the tissue graft appropriate to the physiological stimulation of the cell population in that tissue graft; and
14) preserving the now recellularized and reendothelialized graft by methods know in the art of cryopreservation, cold-storage preservation, and/or nutrient-culture preservation, or directly shipping and implanting the graft post recellularizing/reendothializing.

BRIEF DESCRIPTION OF THE DRAWINGS

Preferred embodiments of the invention are shown in the drawings, wherein:

FIG. 10 is a second view (side view) of a second embodiment of the bioreactor showing an aortic valve (1) where the inflatable piston (9g) has been caused to enter the lumen of the valve using minimal pressure entering via inlet (9e). All other attributes of the illustration are as described in FIG. 8.

FIG. 11 is a second view (side view) of a second embodiment of the bioreactor showing an aortic valve (1) where the inflatable piston (2) has been caused to enter the lumen of the valve and inflated to approach the basement membrane (lumen side) of the valve using greater than minimal pressure entering via inlet (9e). All other attributes of the illustration are as described in FIG. 8.

DETAILED DESCRIPTION OF THE PREFERRED EMBODIMENTS

Figure 1:
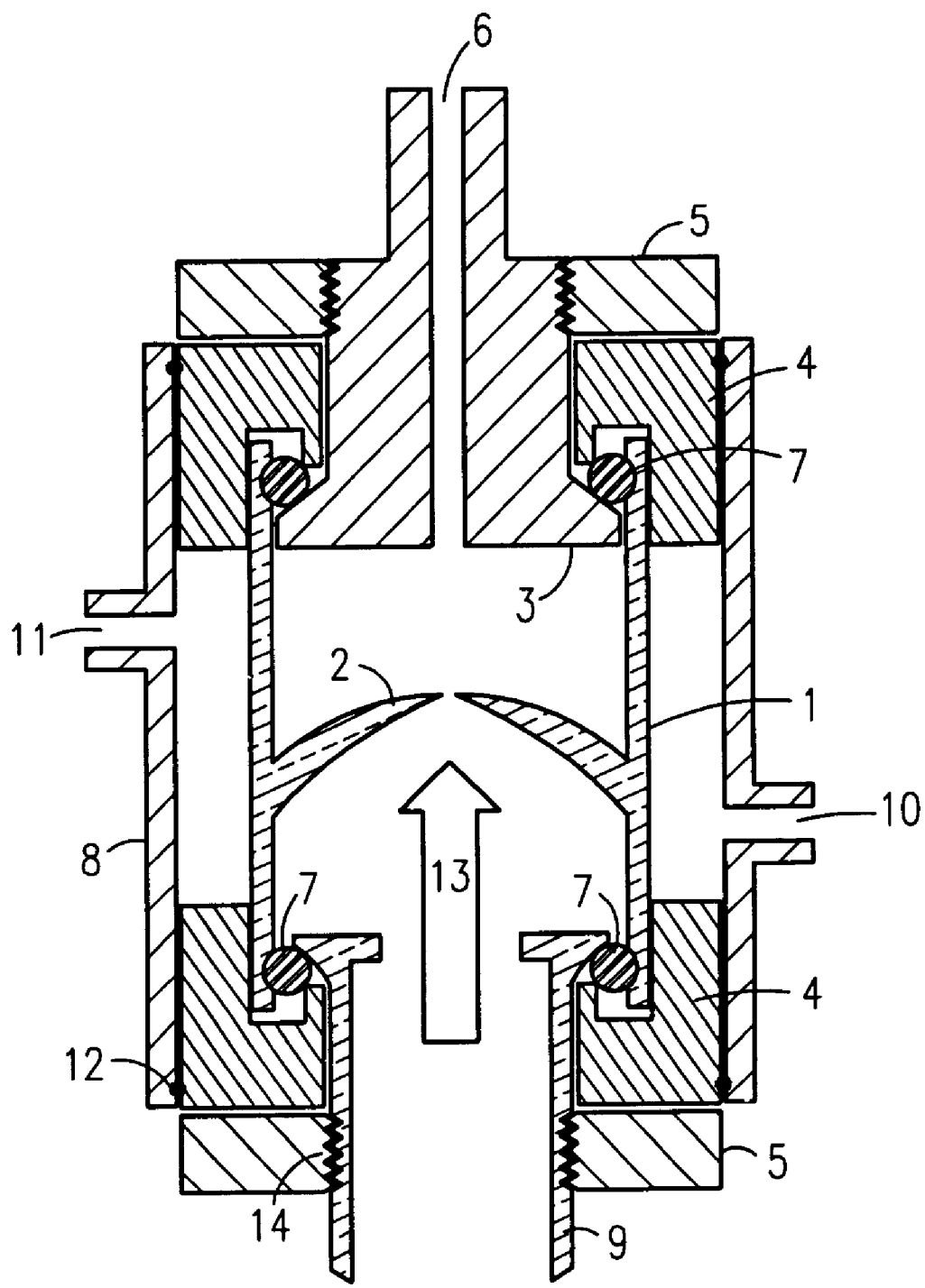
FIG. 1 is a view of one embodiment of the bioreactor showing a heart valve (1) held between inlet (9 and 4) and outlet (3 and 4) end plates and contained within a clear jacket (8) designed to permit washing of the luminal side and adventitial side of the heart valve. This view does not provide details of the inlet end plate, of which one embodiment is provided in FIG. 2. Also shown is a view of one embodiment of the clamping device (7, 4, and 3 and 7, 4, and 9) used to hold the heart valve ends in the clamping ends of the inlet and outlet end plates. Tightening of the knurled nuts (5) as illustrated in FIG. 1 will draw the angled O-ring plates together forcing the O-ring out creating a tight hold on each end of a heart valve against the inside wall of the outer wall of the end plate. This type of clamping mechanism is known in the art of chromatographic columns and is not claimed in the present, patent application as an essential component of a holding mechanism, as the invention contemplates the employment of any suitable holding device. The flow of solutions is shown as arrow (13). The jacket (8) is shown having portals (10 and 11) that are in communication with pulse-dampening chamber (26) that is shown in FIG. 13.
Figure 2:
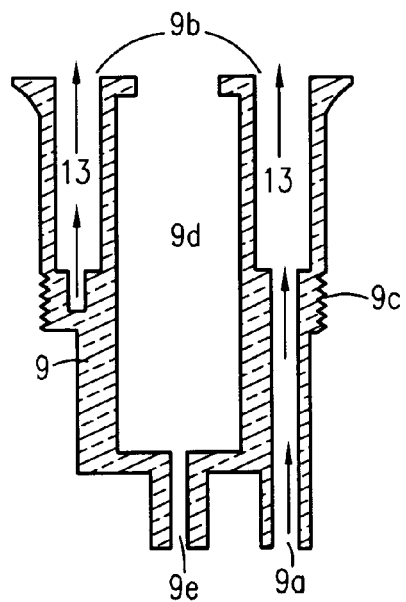
FIG. 2 is a view of one embodiment of one component of the inlet end plate (9) presented to illustrate the chamber of end plate (9d) and the location of an inflatable piston with associated inlet for pressurized gas (9e) and an inlet port (9a) through which solutions and cells may be introduced that will exit through a circumferential opening (9b) into the luminal volume of the tissue being processed. The threads (9c) associated with this embodiment of the inlet end plate will be used in association with the knurled nut (FIG. 1 item 5) to tighten the end plate such that the tissue to be processed will be held tightly to the end plate.
Figure 3:
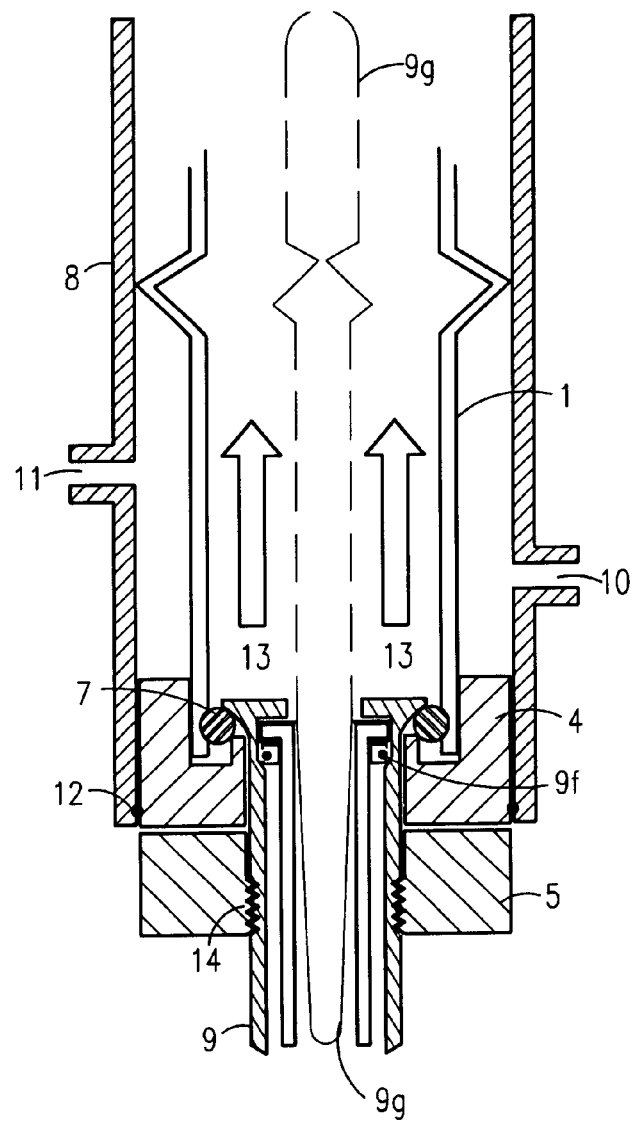
FIG. 3 is a more detailed view of one embodiment of the inlet end plate (4, 9, and 5) and one end of the bioreactor clear jacket (8) showing the position of the inflatable piston (9g) at some minimal pressure. The view is provided to illustrate the difference(s) in solution volumes that may be present in the lumen of a long vascular (artery/vein) tissue (1) contained in the bioreactor during various stages of the processing where it is desired to control the volumes of processing solutions. As illustrated in the dashed line the inflatable piston (9g) will extend into the luminal volume of the tissue allowing change in volumes of solution(s) in the luminal space of that tissue. A small "o" ring (9f) is used to retain the open end of the inflatable piston when placed into this end-plate component (9). The inflatable piston (9g) in this case is a variable length inflatable tube closed at one end such that the tube may be adjusted for length by cutting at the non-closed end and the non-closed end expanded over the piston shaft and held using any suitable clamping mechanism, for example an expandable O-ring (9f). The piston shaft is then inserted into the inlet end plate (9) and the knurled nut (FIG. 1 item 5) used to close the end-plate to the vein/artery segment. The inflatable piston may be inflated using "air" pressure applied at the air pressure inlet (9e, FIG. 2) such that the air moves into the pressure chamber forcing the inflatable piston out of the piston shaft and into the lumen of the artery/vein segment.
Figure 4:
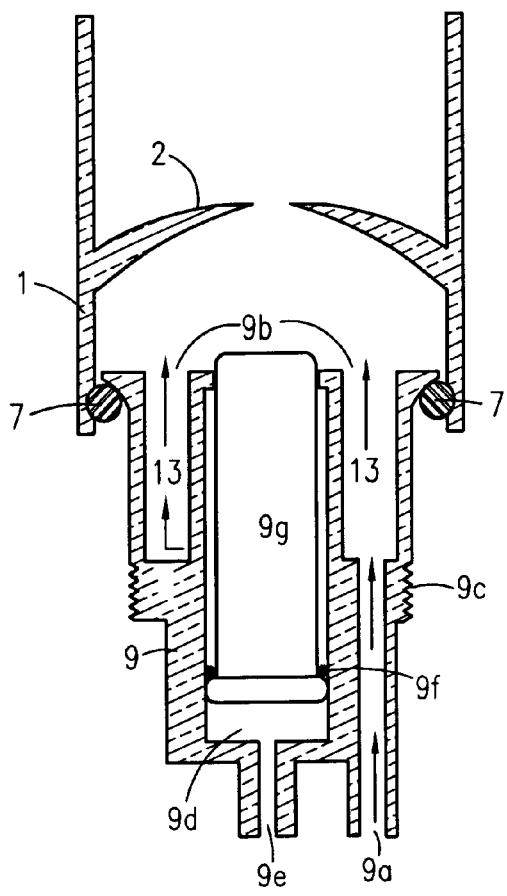
FIG. 4 is a view of one embodiment of the inlet end plate (9) showing the position of the inflatable piston (9g) at some minimal pressure in a chamber of end plate (9d). The view is provided to illustrate the differences in solution volumes that may be present in the lumin of a heart valve (1) contained in the bioreactor during various stages of the processing where it is desired to control the volumes of processing solutions. The inflatable piston is "sealed" using "o" rings (9f) which allow the inflatable piston to move against the inside walls of chamber (9d) of inlet end plate (9). Processing solutions enter via inlet port (9a) and pressure to "air" inflate the inflatable piston enter via inlet port (9e). Threads (9c) are used to tighten the knurled nut (FIG. 1 item 5) to this component of the complete end plate.
Figure 5:
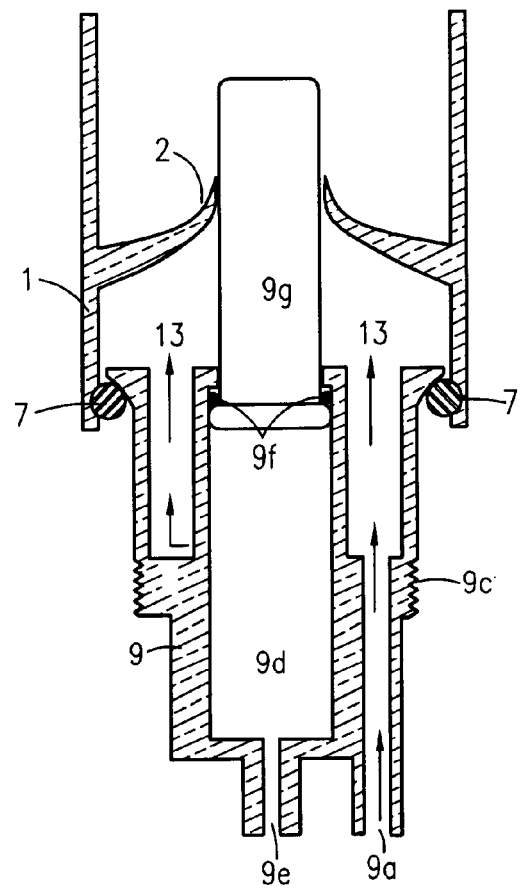
FIG. 5 is a view of one embodiment of the inlet end plate (9) showing the position of the inflatable piston (9g) at some pressure in the chamber of end plate (9d) sufficient to cause the piston to move into the lumen of the heart valve (1). The view is provided to illustrate the differences in solution volumes that may be present in the lumen of a heart valve (1), extending through valve leaflets, contained in the bioreactor during various stages of the processing where it is desired to control the volumes of processing solutions. In this figure the volume in the lumen of the heart valve is less than that illustrated in FIG. 4. The inflatable piston is "sealed" using "o" rings (9f) which allow the inflatable piston to move against the inside walls of chamber (9d), illustrating formation of a tight seal at the end of chamber (9d). Processing solutions enter via inlet port (9a) and pressure to "air" inflate the inflatable piston enter via inlet port (9e). Threads (9c) are used to tighten the knurled nut (FIG. 1 item 5) to this component of the complete end plate.
Figure 6:
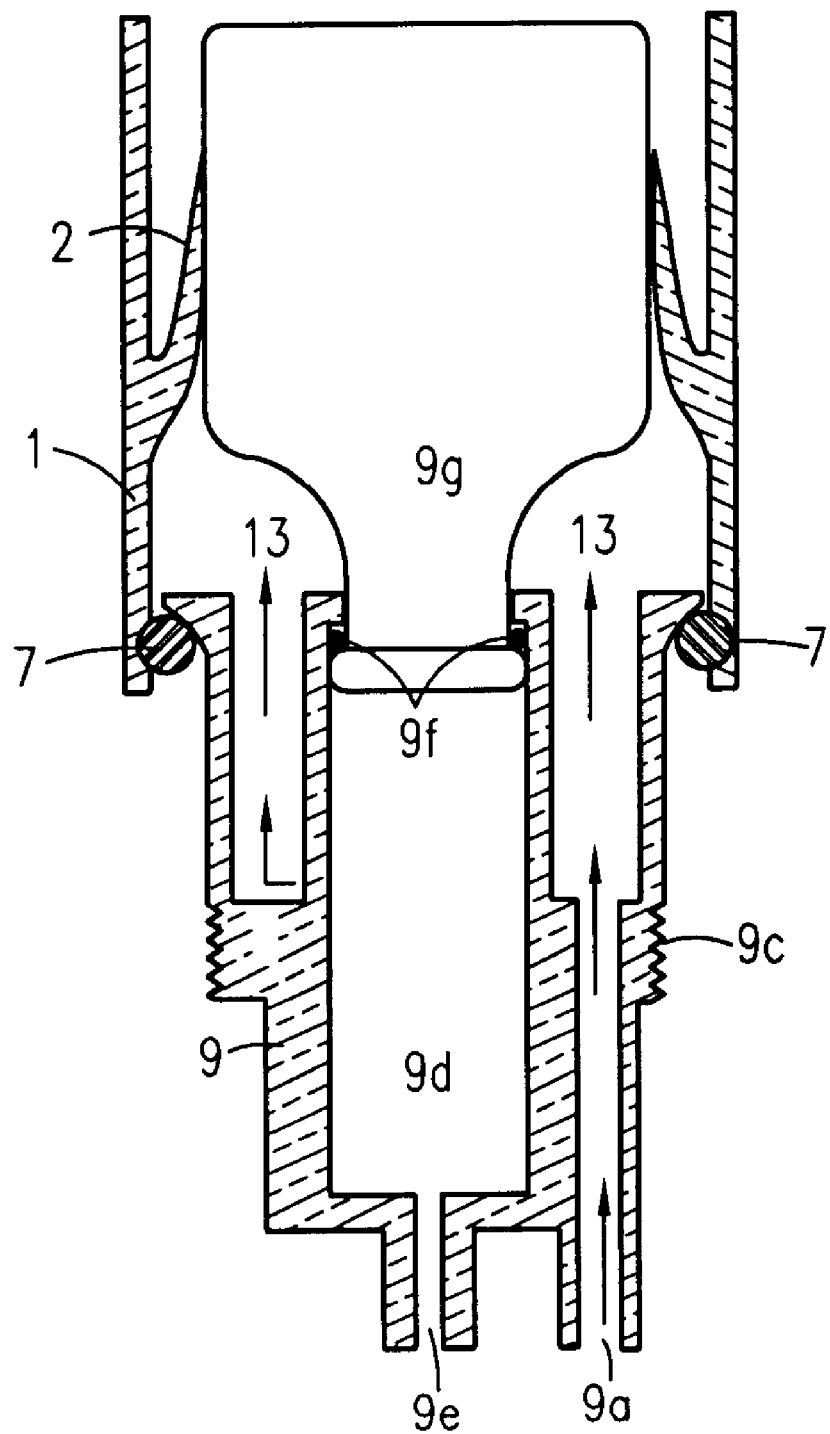
FIG. 6 is a view of one embodiment of the inlet end plate (9) showing the position of the inflatable piston (9g) at some pressure in the chamber of end plate (9d) sufficient to cause the piston to move into the lumen of the heart valve (1) and extend through valve leaflets. This pressure is sufficient to cause the piston to extend and to be inflated to a position where the outside walls of the inflatable piston almost touch (or touch) the inside wall of the heart valve (1). The view is provided to illustrate the differences in solution volumes that may be present in the lumen of a heart valve (1) contained in the bioreactor during various stages of the processing where it is desired to control the volumes of processing solutions. In this figure, the volume in the lumen of the heart valve is less than that illustrated in FIG. 5. The inflatable piston is "sealed", using "o" rings (9f), which allow the inflatable piston to move against the inside walls of chamber (9d) illustrating formation of a tight seal at the end of chamber (9d). Processing solutions enter via inlet port (9a) and pressure to "air" inflate the inflatable piston enter via inlet port (9e). Threads (9c) are used to tighten the knurled nut (FIG. 1 item 5) to this component of the complete end plate.
Figure 7:
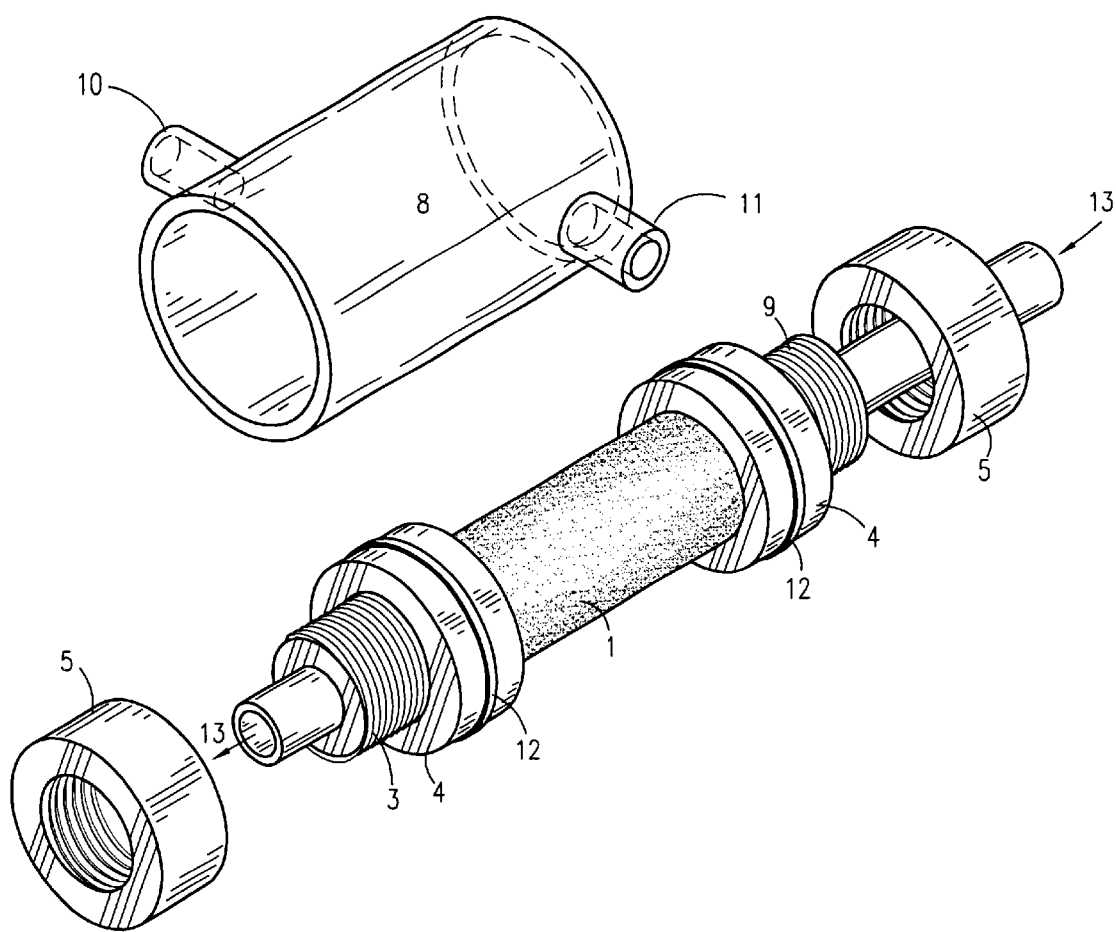
FIG. 7 is one illustration of an "exploded" view of the bioreactor showing the tissue to be processed (1) attached to the inlet and outlet end plates (4) (not differentiated in this illustration). Inlet and outlet ports (3 and 9) (not differentiated in this illustration) are tightened to hold the tissue using knurled nuts (5). The "o" rings (12) used to seal the clear jacket (8) are of sufficient dimension as to allow sliding of the clear jacket over the outsides of the end plates during final assembly permitting positioning of the clear jacket inlet and outlet ports (10 & 11) to clear the end plates.

The bioreactor used in this invention is intended to be used as a closed system to restrict contamination of the vascular grafts material(s) being processed. One of the preferred embodiments of the bioreactor is illustrated in FIG. 1 with details of the inlet end plate illustrated in FIG. 2. The dimensions of the bioreactor may be scaled to accommodate the tissue being processed where the inside diameter of the vascular graft can range between about 3–6 mm (for a small vein or artery graft substitute to as large as 28–35 mm for a pulmonary or aortic heart valve substitute. The essential dimensions are related to the need to allow for expansion of the graft being processed under a maximally anticipated pressure, for example 180 to 200 mm Hg for a valved or non-valved aortic conduit, such that the outside dimension of the graft does not come in contact with the inside wall of the jacket of the bioreactor. Similarly, the essential dimension of the inflatable piston may be such that during some minimal processing pressure, for example about 30 mm Hg for a valved or non-valved aortic conduit, the inside lumin (wall) of the graft does not come in contact with the outside dimension of the inflatable piston. Similarly, the graft holding O-ring mechanism must be small enough to allow the graft to be positioned up and over the O-ring such than a small suture line may be used to secure the graft prior to expansion of the O-ring gripping mechanism, if desired, yet small enough to allow the O-ring gripping mechanism to firmly pinch and hold the graft onto the inlet and outlet end plates. Optionally, fibrin glues, or similar such biologically compatible glues as known in the art, may be used to secure a leak-proof seal of the vascular tissue to the device. Where the graft is of insufficient length to permit attachment, sewing rings consisting of materials known in the art, may be used to extend the suturable/attachable dimensions of tissues to permit attachment to the "end plates" of the bioreactor(s).The inlet port on the inlet end plate must be of sufficient inside diameter to allow a physiological flow rate of processing solutions, yet provide for an even distribution of fluid flow into the luminal volume of the graft being processed. The outlet port of the outlet port plate must be of sufficient inside diameter to allow a physiological flow rate of processing solutions to exit the bioreactor. The inlet and outlet ports of the jacket of the bioreactor should be of a large enough inside diameter to permit the inflow of solutions without creating turbulence on the adventitial side of the graft being processed. The means of creating these dimensions are known to one skilled in the art of manufacturing and the means of manufacturing are not claimed within the context of this invention. The materials comprising the bioreactor are preferably sterilizable using industry standards and could consist of solvent and heat resistant organic polymers manufactured by an injection molding process or of a metallic material manufactured by standard milling processes. Ideally, the bioreactor would be a disposable, single-use, device, but its design and construction would accommodate being taken apart, cleaned, reassembled, and sterilized prior to reuse.

Figure 8:
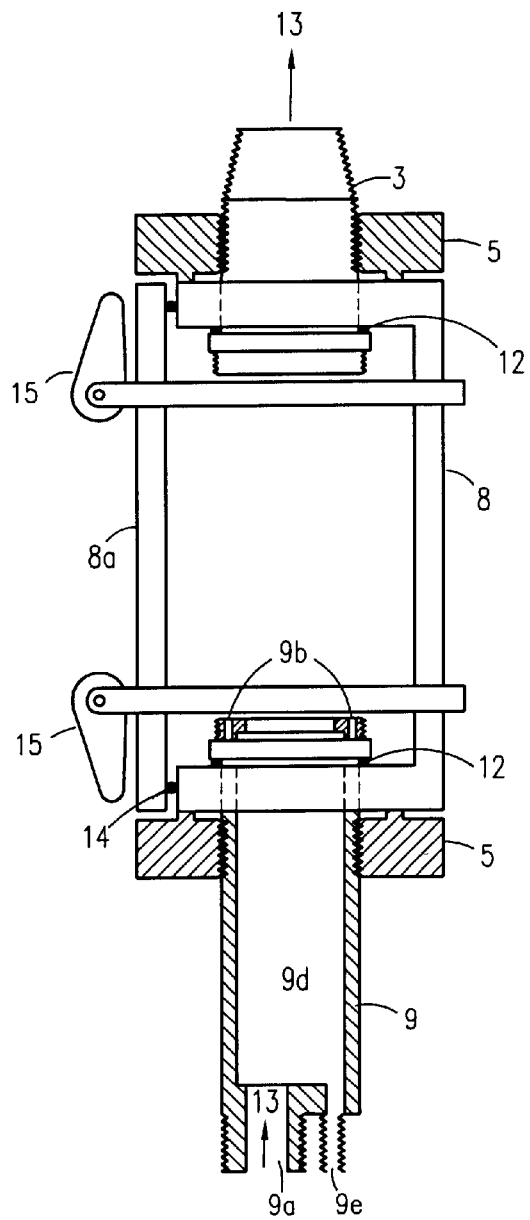
FIG. 8 is a view (side view) of a second embodiment of the bioreactor where the chamber of the bioreactor (8) consists of a, preferably, clear 5 sided rectangular box with inlet (9) and outlet (3) end plates in the long ends. In this embodiment, the inlet and outlet ports include an inlet endplate that consists of long flow tube that includes a chamber for the inflatable piston (9d) with the long flow tube locked into the end of the bioreactor using a knurled nut (5) and sealing "o" rings (12). The outlet endplate (3) is shorter than the inlet endplate and also consists of a hollow tube sealed into the end of the bioreactor using a knurled nut (5) and "o" rings (12) to seal the outlet port to the long end of the bioreactor. The "lid" (8a) of the bioreactor is sealed to the bioreactor using clamps (15) and a large "o" ring (14) that fits in a grove around the top side of the bioreactor box. Inlet and outlet ports within the side-walls of the bioreactor for use in washing the adventitial side of the tissues and for allowing pressure outside tissues being processed to pulse to a pulse dampener are not visible in the present side view.
Figure 9:
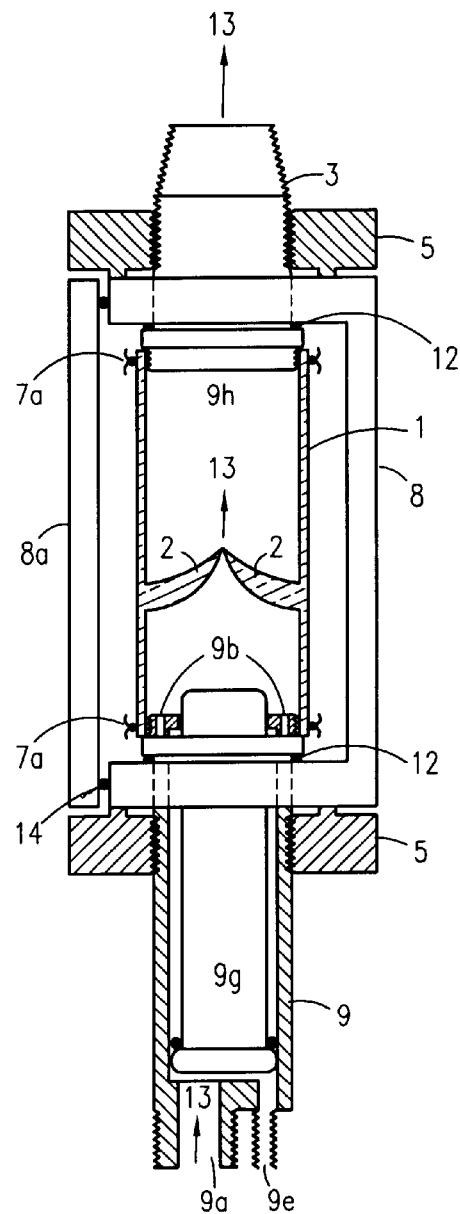
FIG. 9 is a second view (side view) of a second embodiment of the bioreactor showing an aortic valve (1) and an inflatable piston (9g) where the tissue is attached to the inlet (9) and outlet ports (3) using simple sutures (7a) to tie the tissue to the ridged ends on the inlet and outlet ports. In this illustration, the inflatable piston remains positioned in the chamber of the inlet port such that processing solutions may enter via (9a) and exit into the lumen of the valve at (9b). All other attributes of the illustration are as described in FIG. 8.
Figure 12:
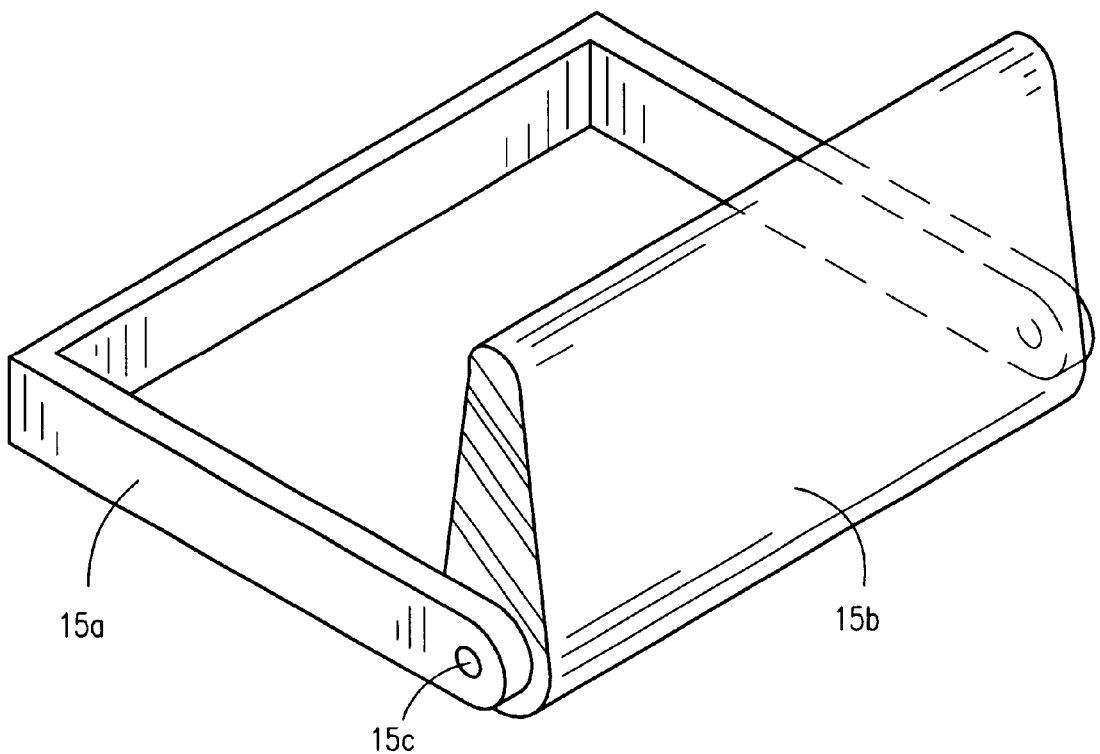
FIG. 12 is a view of the clamping device (15) used to affect closure of the bioreactor illustrated in FIG. 8, a second embodiment of the bioreactor. The position of the pin (15c) on the locking flange (15b) is off-center to allow compression of the top of the bioreactor to the body of the bioreactor as illustrated in FIG. 8 using loop (15a) (clamp closest to the inlet port is open and clamp closest to the outlet port is closed).
Figure 13:
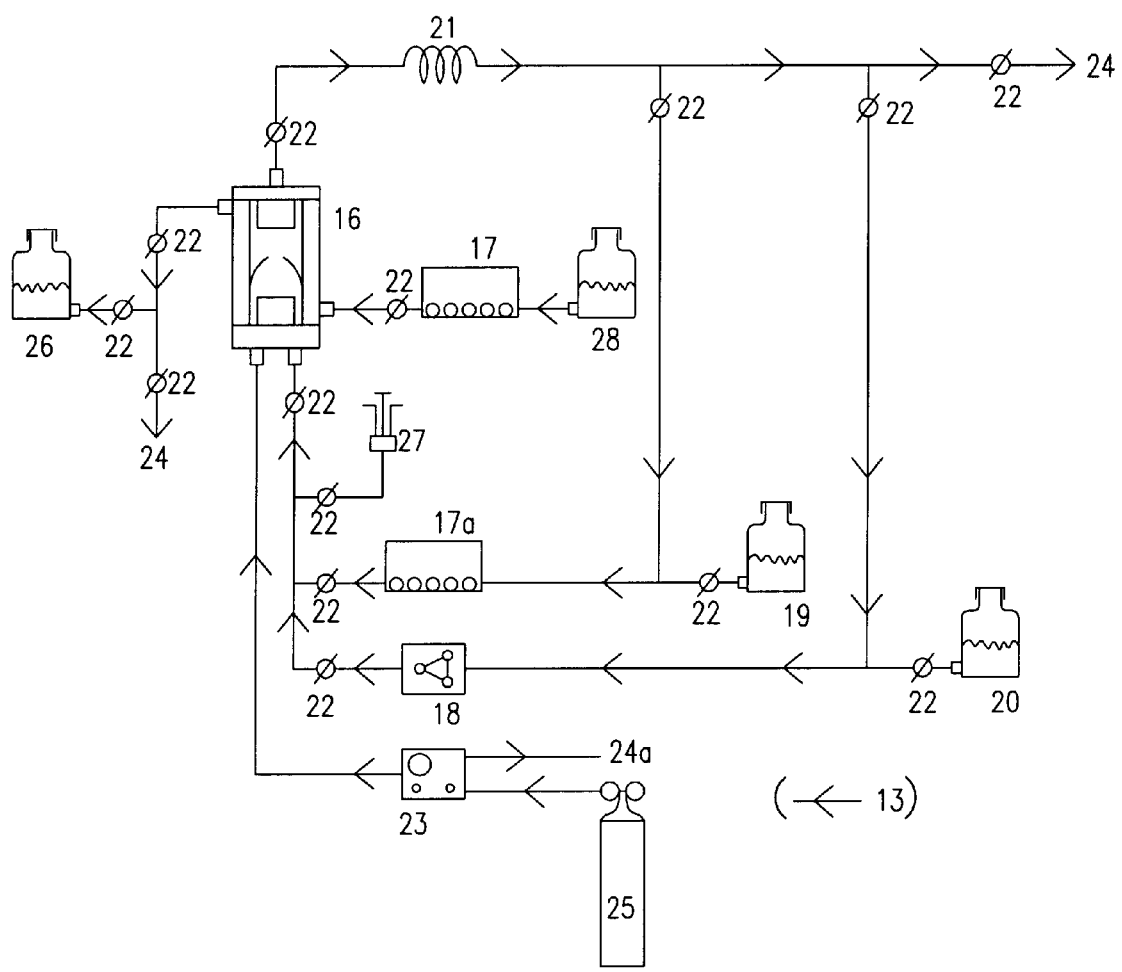
FIG. 13 is a view of one embodiment of a flow diagram provided to illustrate how the flow of various processing solutions are directed to the bioreactor. This flow, using valves (22), peristaltic (17) and pulsatile pumps (18), in-line filters (not shown), solution reservoirs (19, 20, and 28), waste containers (24), and flow restricters (21) is indicted using arrows (13). Enzymes and reagents may be injected into the bioreactor (16) using the "syringe" inlet port (27). The solutions in reservoir (28) may be pumped, using a peristaltic pump (17), into the bioreactor volume outside the luminal volume of the tissue being processed exiting to the pulse-dampening chamber (26) or to waste (24). The solutions in reservoir (19) may be pumped, using a peristaltic pump (17a) into the luminal volume of the tissue being processed exiting to the flow restricter (21) being recycled via the flow diagram illustrated (returning to the peristaltic pump (17a)) or exiting to waste (24). For tissue conditioning, pulsative flow rates may be achieved through the graft lumen using the pulsatile pump (18), pumping solutions from reservoir (20) with such solutions being directed to waste (24) or recycled via the flow route indicated as returning to the pulsatile pump. For pulsatile pumping and graft conditioning a flow restrictor will be added to permit flow of greater fluid volumes. The pressurized gas (25) will be used to inflate the inflatable piston component of the bioreactor using pressure regulator (23) and the inflatable piston deflated via exit port (24a).

The process of recellularization and reendothelialization of a vascular graft, for example an aortic heart valve as described herein, may be described in general terms. The vascular graft may be procured from a human or animal source and transported to the processing facility in a hypotonic solution, in a sterile bag, on wet ice. Once at the processing facility the tissue would be trimmed of excess muscle and fat, the proximal and distal ends cut smoothly, perpendicular to the long axis of the tissue, and/or optionally attaching to sewing rings, and mounted into the tissue holding O-ring constraints on the inlet (4, 9, and 5) and outlet (3, 4, and 5) end plates, respectively (as illustrated in FIG. 1). The clear jacket (item 8, FIG. 1) would be applied and the graft extended to its natural length. If the tissue is an aortic heart valve, proper alignment of the vascular tissue may be checked for valve compliance by filling the outflow side of the valve (using the outflow port (item 6 of FIG. 1) of the outlet end plate (item 3 of FIG. 1) (distal to blood flow) and observing for leaks past the valve leaflets. A compliant valve should not leak. The bioreactor may then be attached to its inlet (item 9a, FIG. 2) and outlet lines that are already attached to the various solvent containers (items 6, 7 and 8; FIG. 8) and waste containers as illustrated in FIG. 13. Subsequent processing is divided into separate phases for purposes of description herein, however, the process is intended to be continuous and may incorporate each described part of the overall process.

Decellularization/Devitalization: If the tissue has not already been decellularized, or was not acellular following construction, the inflatable piston may be caused to enter into the luminal volume of the tissue and inflated to approximately fill the luminal volume. A HEPES buffered (pH 6.0 to 7.5) hypotonic solution of non-ionic detergent(s), for example Brij-35 at 0.2 to 1.0 mM, preferably containing the commercially available Benzonase™, or other suitable enzyme preparations of DNase and RNase, may be pumped into the luminal space of the graft through the inlet port of the inlet end plate and into the volume between the adventitial side of the graft and the jacket through the inlet port of the jacket. These fluids are allowed to exit the bioreactor via the outlet port in the jacket and the outlet port of the outlet end plate, returning to the peristaltic pump (9) for recirculation back into the bioreactor. In-line filters may optionally be used to remove particulate materials from the circulating solution, and this recirculation of decellularization solution may be allowed to proceed for between three (3) and twelve (12) hours at temperatures between 20° C. and 37° C. Decellularization may be monitored at 260 nm for degradation products of the nucleic acids present in the cells being solubilized and degradation of cellular macromolecules. In a preferred aspect, the flow rates of decellularization solutions will be maintained such that a slight positive pressure exists in the luminal volume of the tissue being decellularized. Alternatively, a cellular (vital) tissue may be devitalized using methodologies known in the art. Devitalization may thus be achieved using chemical, physical, or biological means such that the resident cell population is rendered unable to proliferate, becoming reproductively nonvital, or unable to perform necessary metabolic functions, becoming metabolically nonvital. Examples of chemical, physical, and/or biological methods that may be used to render a tissue nonvital would include, but not be all inclusive, extremes of pH, chemicals that irreversibly modify nucleic acids such as deoxyribonucleic acids, membrane perturbants, detergents, solvents such as dimethylsulfoxide that aid to solubilize membranes, apoptosis inducing agents, and alcohols.

Washing: When decellularization and/or devitalization has been completed, the decellularization/devitalization solution is preferably washed from the bioreactor, tissue, and tubing by switching processing solutions to preferably endotoxin-free ultrapure water, however various buffered salt solutions, made hypotonic or hypertonic, may be substituted as required to remove residual cellular elements, and diverting the effluent solution flow to waste. Washing volumes preferably involve volumes in excess of 10 volume changes of the bioreactor volume.

Treatment: The treatment phase of the process is optional, but desirable. The treatment phase of the process involves recirculation flow of aqueous solutions into, through and around the tissue in the bioreactor. This recirculation flow involves flow of solutions through both the luminal and adventitial (i.e. volume between the adventitial surface of the tissue and the jacket) volumes. Treatment solutions, for purposes of this specific process include, but are not restricted to, low ionic strength HEPES (or similar Good buffer) buffered (pH 6.5–7.4) aqueous solutions of fibroblast growth factor (0.1 nM to 0.1 $\mu$M), thapsigargin (0.001 mM to 1.0 mM), suramin (0.001% to 1.0% by weight), sodium dodecylsulfate (0.001% to 1.0% by weight), bone morphogenetic protein(s) 1, 2, 6, and 7 (0.01 nM to 0.1 $\mu$M), aggrecan (0.0001% to 0.01% by weight), hyaluronins (0.0001% to 0.1% by weight), interleukin 6 (0.001 nM to 0.1 nM), glutathione ethylester (or glutathionine), and/or transferin. Recirculation volumes may be minimized by inserting and inflating the inflatable piston in the luminal volume of the graft.

Washing: When optional treatment has been completed, the treatment solution(s) is (are) washed from the bioreactor, tissue, and tubing by switching processing solutions to preferably ultrapure water, optionally supplemented with glutathione ethylester, however various buffered salt solutions or alcohol solutions may be substituted as required to remove residual cellular elements and treatment agents, and diverting the effluent solution flow to waste. Washing volumes preferably involve volumes in excess of 10 volume changes of the bioreactor volume.

Basement Membrane Removal/Perforation: With the inflatable piston in the inflated position, buffered solutions/suspensions of proteolytic and/or hydrolytic enzymes may be injected through the sample inject (item 5; FIG. 13) and pumped into the luminal volume of the tissue via the inlet port of the inlet end plate. During this process, the outlet port of the outlet end plate needs to be opened. When the volume present in the luminal volume of the tissue has been replaced by the proteolytic solution, the inlet port and outlet ports of the inlet and outlet end plates may be closed. For this step of the process, both the inlet and outlet ports of the jacket preferably remain in the closed position. The proteolytic enzymes that may be used in this step of the process include trypsin, chymotrypsin, elastase, collagenase, dispase, ficin, papain, and/or alkaline protease. The hydrolytic enzymes that may be used in this step of the process include hyaluronidase, glucuronidase, and/or neuraminidase. The enzymes may be free in solution or attached to microscopic beads, such that hydrolysis of basis membrane will occur only where these microscopic beads, to which hydrolytic enzymes are tightly attached, come in physical contact with the basement membrane. See, for example, immobilized papain, pepsin, trypsin as attached to cross-linked 6%/4% beaded agarose and available from Pierce Chemical Company (product numbers 20341ZZ, 20343ZZ and 20233ZZ, respectively). Alternatively, specific bacterial species which produce and secrete specific hydrolytic enzymes, for example, *Clostridium histolyticum* for collagenase, *Bacteroides gingivalis, Fusobacterium nucleatum, Actinobacillus actinomycetemcomitans,* and/or mammalian cells such as U937 monoblastoid cells, and/or an oral flagellate such as *Trichomonas tenax,* may be used instead of the microscopic beads (to which hydrolytic enzymes are attached) to digest holes in the basement membrane. This step in the process is intended to be of only sufficient time to permit digestion of a significant portion of the basement membrane (that membrane to which the endothelial cells attach in a native tissue) to allow penetration of the fibroblastic cell population into the matrix structure yet leave sufficient basement membrane to facilitate subsequent re-endothelialization. The time intervals, enzymes, enzyme concentrations, and buffer conditions will be dictated by the type of graft being treated and the condition of the basement membrane of the tissue at the time of treatment. For example, for an aortic valve denuded of endothelial cells during the initial cold transport in hypotonic solutions, an appropriate enzyme concentration and time might include, but not be limited to, the enzyme collagenase at 0.01 lU/ml to 1.0 lU/ml for periods of time between 30 to 180 minutes. Times that may be expected to achieve the desired digestion of basement membrane in a typical aortic heart valve. For aortic valves retaining a significant endothelial cell layer, dispase (0.01 lU/ml to 0.5 lU/ml) may need to be added to the collagenase solution to help remove the endothelial cells permitting access of the collagenase to the basement membrane. Use of trypsin, chymotrypsin, elastase, ficin, papain, and/or alkaline protease may be used to enhance basement membrane digestion, however they may also be expected to degrade the underlying tissue matrix if incubation times are greater than 30 to 60 minutes. Incubation temperatures may be between 20° C. and 37° C. By regulating the size(s) of the microscopic beads, or bacterial species, it is possible to not only control the size(s) of the holes created in the basement membrane, but to control the number of holes per unit surface area of the basement membrane by controlling the density of the microscopic beads (bacteria) used in the treatment solution.

Washing: It is essential that the proteolytic and hydrolytic digestion of the basement membrane be terminated quickly and efficiently. Towards this end, washing of the tissue to terminate removal of the basement membrane may be accomplished at reduced temperatures, for example 0° C. to 5° C., with rapid flow of buffered (pH 5.0 to 6.0) water solutions through both the luminal and adventitial volumes of the bioreactor. By maintaining a slightly positive pressure differential from the adventitial to luminal side of the graft, microscopic beads may be induced to dislodge from the luminal side of the graft and move into the flow of washing solution(s). Flow of these washing solutions may be directed to waste. Wash volumes preferably are in excess of 20 bioreactor volumes over a time interval of 30 to 180 minutes.

Fibroblast Cell Seeding: Fibroblast cell seeding through the sample injection port (5) (FIG. 13) into the luminal volume of the tissue may be accomplished following removal (perforation) of the basement membrane. To accomplish this cell seeding, several approaches may be used according to the principles of the invention. In one approach, the inflatable piston is present in the luminal volume of the graft and in an alternative approach the inflatable piston is not present in the luminal volume of the graft. In both approaches, positive pressure (luminal to adventitial side of the graft) may be used to induce movement of the fibroblast cells into the tissue matrix. The fundamental differences in how this positive pressure is applied constitutes the essential difference in these two approaches.

When the inflatable piston is present in the luminal volume of the graft, fibroblast cells (obtained from either primary tissue digests of the intended recipient of the graft (autograft cells) or from fibroblastic cells maintained in tissue culture (allograft/xenograft cells)) will be pumped into the luminal volume of the graft via the inlet port of the inlet end plate. During the initial stages of delivery of the cells into this luminal volume, the outlet port of the outlet end plate will be open and the inlet and outlet ports of the jacket will be closed. The fibroblast cells will be at total viable cell numbers between $1 \times 10^6$ and $1 \times 10^8$ cells/tissue to be recellularized. The total number of cells to be infused into the matrix of a specific tissue will approximate 1000 to 10,000 cells/mm$^3$ of tissue matrix. Once the cells have been delivered into the luminal volume of the tissue, the outlet port of the outlet end plate may be closed and the outlet port of the jacket opened (with flow directed to waste). The flow rate on the peristaltic pump may be reduced to achieve a minimal positive pressure in the luminal volume of the tissue. Solution being pumped may be switched from a cell suspension to a nutrient and growth factor-rich tissue culture medium supplemented with glutathione ethylester (or similar antioxidant) and/or similar anti-apoptotic agents such as IGF-1, calpastatin, or caspase inhibitors such as ZVAD-fmk (z-val-ala-asp(OME)CH$_2$F; caspase-I and II inhibitors), caspase-1 inhibitor and calpain inhibitors (for example N-Ac-Leu-Leu-norleucinal and N-Ac-Leu-Leu-Methional), but not supplemented with serum. Flow of this nutrient solution may be maintained for between 3 to 12 hours, or until cells may be detected in the outflow solution from the bioreactor, at 37° C. After about 12 hours, flow of nutrient may be directed out of the luminal volume of the tissue via the outlet port of the outlet end plate to waste.

When the inflatable piston is not present in the luminal volume of the graft, fibroblast cells (obtained from either primary tissue digests of the intended recipient of the graft (autograft cells) or from fibroblastic cells maintained in tissue culture (allograft cells)) may be added via the sample inject (5) (FIG.13) and pumped into the luminal volume of the graft via the inlet port of the inlet end plate. During the initial stages of delivery of the cells into this luminal volume, the outlet port of the outlet end plate will preferably be open and the inlet and outlet ports of the jacket will preferably be closed. The fibroblast cells will be at total viable cell numbers between $1 \times 10^6$ and $1 \times 10^8$ cells/tissue to be recellularized. The total number of cells to be infused into the matrix of a specific tissue will approximate 1000 to 10,000 cells/mm$^3$ of tissue matrix. Once the cells have been delivered into the luminal volume of the tissue, the outlet and inlet port of the outlet and inlet end plate may be closed and the outlet port of the jacket opened (with flow directed to waste). Pressure may be slowly applied to the inflatable piston to create a positive pressure in the luminal volume of the tissue sufficient to distend the tissue. As the cell suspension volume becomes less, additional pressure may be applied to the inflatable pistons to maintain the positive pressure and flow of solution in the luminal volume to the adventitial side of the tissue. When it is determined that the cell volume has been significantly diminished and cells have penetrated into the matrix spaces, the inlet and outlet ports of the inlet and outlet end plates may be opened, and nutrient solution not containing serum (as described above) may be pumped into, through, and out of the bioreactor being directed to waste.

Reendothelialization of the Tissue: Following removal of the fibroblastic cell population from the luminal volume of the graft, endothelial cells may be mixed into a viscous, collagenous/non-collagenous, solution at total cell numbers calculated as necessary to cover the luminal surface of the graft being reendothelialized. Such total cell numbers may be calculated by anyone skilled in the art and knowing the surface area typically covered by an endothelial cell in a native vascular graft. The collagenous/noncollagenous solution will include antioxidants such as glutathione ethylester in nutrient medium and collagen primarily of type IV, derived by extraction of tissues or as a recombinant product, however other collagen types (for example, types I, II, V, VII and X) may be included as desired. The concentration of collagen may range between about 0.01% and 2% by weight. The endothelial cells may be derived as primary cultures from the intended recipient of the tissue graft (an autograft approach) or from endothelial cell cultures derived from cell banks (an allograft/xenograft approach) which may or may not have been genetically manipulated to reduce immunogenicity or improve paracrine functions. In that endothelial cells express MHC antigens, an allograft approach to seeding of enthothelial cells would not be expected to be retained on the luminal surface of a reendothelialized graft for extended periods of time post transplantation unless such cells have been genetically manipulated to render them nonimmunogenic to the recipient.

Endothelial cells present in a collagenous/noncollagenous solution, to increase solution viscosity and cell adhesion may be injected into the system via the sample inject (5) (FIG. 13) and pumped into the luminal volume of the tissue contained in the bioreactor via the inlet port of the inlet end plate. During this process, the outlet port of the outlet end plate is opened, and the inflatable piston is extended into the luminal volume of the tissue and inflated to a distance between 2 and 5 mm from the luminal surface of the tissue. The inlet and outlet ports of the jacket may be closed during this step of the process. The viscous collagenous/ noncollagenous mixture of endothelial cells may be pumped into the volume between the tissue and the inflatable piston and the outlet and inlet ports of the outlet and inlet end plates may be closed. Pressure may be then slowly applied to the inflatable piston until the outside wall of the piston reaches the inside wall of the lumen of the tissue. If necessary, pressure may be released and reapplied as needed to evenly distribute the collagenous cell mixture evenly between the inflatable piston and the luminal surface of the tissue. At a specified point in this process, the increase in pressure with time may be stopped and a pressure sufficient to maintain the piston wall in contact with the lumen wall is preferably maintained for between 1 and 6 hours. The temperature during this process is preferably maintained at 37° C. At the end of this incubation period, the inlet and outlet ports of the inlet and outlet end plates may be opened and nutrient medium may slowly pumped into the luminal space of the tissue while the pressure on the inflatable piston may slowly reduced. The objective is to have the pressure induced flow of the nutrient medium begin to "peel" the inner luminal surface of the tissue from the inflatable piston at the "proximal end" of the tissue and to have this "peeling" process proceed towards the "distal end" of the tissue. Flow of nutrient medium through the luminal volume of the tissue may be slow and the eluent monitored for fragments of collagen/endothelial cells. If fragments appear in the eluent, the inflatable piston may be reinflated and incubation continued for a time period necessary to cause the collagen/ endothelial cell mixture to adhere to the tissue.

The recellularized and reendothelialized tissue may be incubated at 37° C. for between 12 and 24 hours with a slow flow of nutrient and growth factor enriched HEPES buffered tissue culture medium supplemented with glutathione ethylester (or similar antioxidant), anti-apoptotic agents such as, for example, IGF-1 and/or ZVAD-fmk (a caspase inactivator), fetal calf or recipient serum (or similar serum substitute if use of a serum-free medium is desired) and selenium/transferin as known to anyone skilled in the art of tissue culture additives. Flow rates may be determined by one skilled in the art of monitoring eluent medium for glucose, lactose, ammonia, etc., such that metabolic states of the cells may be determined and flow rates either increased or decreased according to nutrient depletion and/or waste product accumulation.

Graft Conditioning: Prior to transplantation, it may be desirable to precondition the graft by subjecting it to high pressure pulsatile flow of nutrient and growth factor enriched HEPES (or similar non-toxic) buffered tissue culture medium, at 37° C., supplemented glutathione ethylester (or similar antioxidant) and anti-apoptotic agents, for example IGF-1 and/or ZVAD-fmk (a caspase inactivator), with fetal calf or recipient serum (or similar serum substitute if use of a serum-free medium is desired) and selenium/transferin. The pressure and pulsatile flow patterns may be adjusted to simulate those pressures and pulsatile flow patterns to be found in the site in which the graft is to be implanted. The outlet port of the jacket may be open with flow of solution contained in the space between the tissue graft and the jacket directed to a pulse-dampening device to control the application of stress, and strain, to the graft. During this preconditioning, eluent solution may be monitored for fragments of collagen/endothelial cells. These will appear as particulate materials in the outflow side of the graft. Preconditioning times will vary with tissue graft type and desired alignment and orientation of the endothelial cells covering the luminal surface of the graft. Preconditioning is primarily directed at causing release of any collagen/endothelial cell fragments that will be release and to stimulating cell to cell interactions essential to long-term function and maintenance of a viable cell population in the tissue graft.

Cell Selection: Recellularization and reendothelialization of an acellular vascular graft may reasonably be expected to occur under the conditions described. However, it is important that the appropriate type of fibroblastic and endothelial cell population be selected for the recellularization/reendothelialization events. All cells, with the exception of reproductive cells such as eggs and sperm, are omnipotent, i.e. contain the same complement of genes and genetic material. However, some cells are more differentiated towards a given phenotype than other cells and there exists within fibroblastic cell populations in a body, fibroblastic cells with differing degrees of differentiation towards a specific phenotype. For example, there exist fibroblastic cells designated as myofibroblasts, based on tissue of origin, and these myofibroblasts may originate from aortic conduit tissue, myocardium, or similar contractile tissues. In that proper growth and differentiation factor mediated cell stimulation may be used to direct, or redirect, cell growth and differentiation, origin of a fibroblastic cell population to be used in recellularization of a cardiovascular tissue is less important than preventing triggering of a programmed cell death process commonly referred to as "apoptosis". Morphologically, apoptosis is characterized by chromatic condensation, cell shrinkage, and membrane blebbing. Within the cell, various proteases and endonucleases are activated leading to degradation of protein and nucleic acids. This is in contrast to the other mode of cell death, necrosis, which is uncontrolled in nature and is characterized by swelling and lysis of the cell. Oxidative stress is potentially a common signaling mechanism among diverse inducers of apoptosis and thus the inclusion of antioxidants or other agents such as IGF-1 and/or ZVAD-fmk (a caspase inactivator) in the processing and nutrient culture medium solutions described in this invention represents an important element of recellularization/reendothelialization designed to restrict programmed cell death in these tissues post-transplantation. Glutathione ethylester is a strong antioxidant that is freely permeable into cells. It is theoretically and practically possible to genetically manipulate cells used in repopulation of cardiovascular tissues to restrict apoptosis by enhancing activity of genes acting as promoters (e.g. bax, Fas, and p53) and effectors (ICE-like proteases) or inhibitors (e.g. bcl-2, bcr-abl) of the process. Bcr-abl may be an activated form of a gene that is antiapoptotic.

Thus, although the present invention is not directed towards use of specific fibroblastic or endothelial cells derived from specific tissues, it is an important aspect of the present invention to use metabolically and reproductively viable cell populations and to include in the various nutrient and processing solutions, additives which enrich the metabolic functions of these cells and which serve to restrict induction of the process of apoptosis until the cell populations may be properly oriented and stimulated, both mechanically and chemically, to resume proper cell to cell communication essential to long-term viability and function. Initial stimulation of the endothelial cells used to construct a new basement membrane or fill the holes in the basement membrane formed from the microscopic bead containing hydrolytic enzymes may occur via addition of fibroblast and/or vascular endothelial cell growth factor(s) into the nutrient medium. In addition, however, platelets from the intended recipient, or donor-derived platelets, may be used to treat the newly constructed basement membrane. Addition of platelets to the bioreactor following inflatable piston compression of the collagenous/noncollagenous/endothelial cells construct will result in platelet aggregation and activation by the "rough" protein structure. This platelet aggregation and activation will serve a similar purpose as addition of fibroblast or vascular endothelial cell growth factor to the nutrient medium, or preaddition to the construct, and will localize delivery of essential growth and differentiation factors at the site on the new basement membrane where it is desired to have a smooth layer of overlapping and function endothelial cells.

What is claimed:

1. A device for producing a recellularized, reendothelialized, vascular tissue graft comprising:
    a jacket having an interior;
    inlet and outlet plates removably attached to said jacket at opposed ends, said inlet and outlet plates adapted to removably retain the graft at opposed ends;
    an inlet port disposed in said inlet plate and an outlet port disposed in said outlet plate, said inlet and outlet ports in communication with the interior of said jacket and permitting the entry and exit of processing streams into and out of the luminal volume of the graft being retained in the device; and
    an inflatable piston adapted for insertion into the interior of said jacket and located to enter the luminal volume of the graft being retained in the device.

2. The device of claim 1, further comprising a piston inlet opening in fluid communication with said inflatable piston.

3. The device of claim 2, further comprising a source of pressurized gas in fluid communication with said piston inlet opening.

4. The device of claim 3, further comprising a pressure regulator disposed between said source of pressurized gas and said piston inlet opening.

5. The device of claim 4, further comprising an exit port in fluid communication with said piston inlet opening for releasing pressure from said inflatable piston.

6. The device of claim 1, wherein the jacket is constructed of an optically clear material.

7. The device of claim 1, wherein the device is sterilizable using conventional methods.

8. The device of claim 1, further comprising inlet and outlet valves attached to said inlet and outlet ports.

9. The device of claim 1, wherein said piston is designed to contact the internal face of the graft.

10. The device of claim 1, further comprising a peristaltic pump in fluid communication with the interior of said jacket through said inlet or outlet port.

11. The device of claim 1, further comprising a pulsatile pump in fluid communication with the interior of said jacket through said inlet or outlet port.

12. The device of claim 11, further comprising a flow restrictor in fluid communication with the interior of said jacket through said outlet port.

13. The device of claim 11, further comprising a syringe inlet port in fluid communication with the interior of said jacket through said inlet port.

14. The device of claim 1, further comprising a pulse-dampening device in fluid communication with the interior of said jacket through a second outlet port provided in communication with a volume defined by the interior of the jacket and an external face of a graft retained in the device.

15. A device for producing a recellularized, reendothelialized, vascular tissue graft comprising:
- a jacket having an interior;
- inlet and outlet plates removably attached to said jacket at opposed ends, said inlet and outlet plates adapted to removably retain the graft at opposed ends;
- a first inlet port disposed in said inlet plate and a first outlet port disposed in said outlet plate, said inlet and outlet ports in communication with the interior of said jacket and permitting the entry and exit of processing streams into and out of the luminal volume of a graft retained in the device;
- a second inlet port and second outlet port disposed in said jacket arranged to be in communication with the external face of the graft; and
- a pulse-dampening device;
- wherein fluid is caused to exit from between said jacket and the external face of the graft via the second outlet port of said jacket to said pulse-dampening device.

16. The device of claim 15, wherein the jacket is constructed of an optically clear material.

17. The device of claim 15, wherein the device is sterilizable using conventional methods.

18. The device of claim 15, further comprising inlet and outlet valves attached to said first inlet and outlet ports.

19. The device of claim 15, further comprising an inflatable piston adapted for insertion into the interior of said jacket and located to enter the luminal volume of the graft being retained in the device.

20. The device of claim 19, further comprising a piston inlet opening in fluid communication with said inflatable piston.

21. The device of claim 20, further comprising a source of pressurized gas in fluid communication with said piston inlet opening.

22. The device of claim 21, further comprising a pressure regulator disposed between said source of pressurized gas and said piston inlet opening.

23. The device of claim 22, further comprising an exit port in fluid communication with said piston inlet opening for releasing pressure from said inflatable piston.

24. The device of claim 19, wherein said piston is designed to contact the internal face of the graft.

25. The device of claim 15, further comprising a peristaltic pump in fluid communication with the interior of said jacket through said first inlet or outlet port.

26. The device of claim 15, further comprising a pulsatile pump in fluid communication with the interior of said jacket through said first inlet or outlet port.

27. The device of claim 15, further comprising a flow restrictor in fluid communication with the interior of said jacket through said first outlet port.

28. The device of claim 15, further comprising a syringe inlet port in fluid communication with the interior of said jacket through said first inlet port.

29. A device for producing a tissue graft, comprising:
- a generally cylindrical body having an open top end and an open bottom end, and a first inlet port and a first outlet port;
- a top end cap comprising a second outlet port having a first diameter, said top end cap in removable communication with said top end of said body to form a liquid tight seal between said body and said top end cap;
- a bottom end cap comprising a second inlet port having a second diameter, said bottom end cap in removable communication with said bottom end of said body to form a liquid tight seal between said body and said bottom end cap;
- means for attaching a top end of a tubular tissue structure to said top end cap at a lower surface of said top end cap and for attaching a bottom end of a tubular tissue structure to said bottom end cap at an upper surface of said bottom end cap to form a tubular tissue structure continuous with the flow of solutions through the said device wherein the second inlet and outlet ports are provided in flow communication with the luminal volume of the tubular tissue structure and the first inlet and outlet ports are provided in flow communication with a volume defined by an interior of the body and external face of the tubular tissue structure; and
- an inflatable piston adapted for insertion into said body and located to enter the luminal volume of the tubular tissue structure being retained in the device.

30. The device of claim 29, further comprising a piston inlet opening in fluid communication with said inflatable piston.

31. The device of claim 30, further comprising a source of pressurized gas in fluid communication with said piston inlet opening.

32. The device of claim 31, further comprising a pressure regulator disposed between said source of pressurized gas and said piston inlet opening.

33. The device of claim 32, further comprising an exit port in fluid communication with said piston inlet opening for releasing pressure from said inflatable piston.

34. The device of claim 29, wherein the body is constructed of an optically clear material.

35. The device of claim 29, wherein the device is sterilizable using conventional methods.

36. The device of claim 29, further comprising inlet and outlet valves attached to said first inlet or outlet ports and said second inlet or outlet ports.

37. The device of claim 29, wherein said piston is designed to contact the internal face of the tubular tissue structure.

38. The device of claim 29, further comprising a peristaltic pump in fluid communication with the interior of said body through said second inlet or outlet port.

39. The device of claim 29, further comprising a pulsatile pump in fluid communication with the interior of said body through said second inlet or outlet port.

40. The device of claim 29, further comprising a flow restrictor in fluid communication with the interior of said body through said second outlet port.

41. The device of claim 29, further comprising a syringe inlet port in fluid communication with the interior of said body through said second inlet port.

42. The device of claim 29, further comprising a pulse-dampening device in fluid communication with the interior of said body through said first outlet port.

* * * * *